(12) United States Patent
Lindström

(10) Patent No.: US 7,195,622 B2
(45) Date of Patent: Mar. 27, 2007

(54) FASTENING DEVICE FOR FASTENING OF ABSORBENT ARTICLES

(75) Inventor: Asa Lindström, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 11/017,064

(22) Filed: Dec. 21, 2004

(65) Prior Publication Data
US 2005/0143709 A1 Jun. 30, 2005

Related U.S. Application Data

(60) Provisional application No. 60/530,989, filed on Dec. 22, 2003.

(51) Int. Cl.
*A61F 13/15* (2006.01)
(52) U.S. Cl. .................. 604/392; 604/389; 604/391; 604/393; 604/394; 604/395; 604/396; 604/399; 604/400; 604/401; 604/402
(58) Field of Classification Search ............... 604/392, 604/391, 393, 394, 395, 396, 399, 400, 401, 604/402, 389
See application file for complete search history.

(56) References Cited

U.S. PATENT DOCUMENTS 2,910,982 A * 11/1959 Woodward ............. 604/385.01
3,335,721 A * 8/1967 Gastwirth ................. 604/391
3,893,460 A 7/1975 Karami
5,304,162 A * 4/1994 Kuen ..................... 604/391
5,445,628 A * 8/1995 Gipson et al. ............ 604/392
6,342,050 B1 1/2002 Ronnberg et al.
6,524,294 B1 2/2003 Hilston et al.
6,579,275 B1 * 6/2003 Pozniak et al. ............ 604/390

FOREIGN PATENT DOCUMENTS

DE 34 40 544 A1 5/1986
EP 0 482 383 A1 4/1992
GB 1 441 567 7/1976

* cited by examiner

*Primary Examiner*—Tatyana Zalukaeva
*Assistant Examiner*—Ginger Chapman
(74) *Attorney, Agent, or Firm*—Buchanan Ingersoll & Rooney PC

(57) ABSTRACT

An absorbent article has a fastening arrangement for fastening the absorbent article. The fastening arrangement is an extendable fastening arrangement formed by the material strip being folded in a Z along two transversely extending fold lines which divide the material strip into a first end portion at the first short end, a second end portion at the second short end, and a middle portion between the end portions. The first end portion of the material strip is secured to the middle portion by a first breakable attachment, and the second end portion of the material strip is secured to the middle portion by a second breakable attachment, and the fastening device is arranged on the second end portion on a surface directed away from the middle portion.

23 Claims, 5 Drawing Sheets

FASTENING DEVICE FOR FASTENING OF ABSORBENT ARTICLES

CROSS-REFERENCE TO RELATED APPLICATIONS

The present application claims the benefit of U.S. Provisional Application No. 60/530,989, filed in the United States on Dec. 22, 2003, the entire contents of which are hereby incorporated herein by reference.

TECHNICAL FIELD

The invention relates to an absorbent article with a longitudinal direction and a transverse direction, and with two end edges extending in the transverse direction and two side edges extending in the longitudinal direction, and comprising a fastening arrangement for fastening the absorbent article, said fastening arrangement comprising a material strip with a longitudinal direction and a transverse direction and with a first short end and a second short end, said first short end of the material strip being firmly anchored in the absorbent article, and the material strip comprising a fastening device.

BACKGROUND

Absorbent articles for absorption of body fluids are available in a number of different designs. For absorption of urine and excrement, use is generally made of diapers or incontinence guards with a shape which, during use, simulates a pair of briefs. Such diapers can of course be designed as one-piece absorbent briefs which are taken off in the same way as a pair of conventional briefs. A design of this kind is, however, best suited for use by persons who are able to stand up and can put the diaper on and take it off themselves. For young children and incontinent adults with reduced mobility and impaired balance, for whom the diaper is usually put on and taken off by a guardian or helper, other types of diapers are often more practical. Another disadvantage of diaper pants is that they have relatively little capacity for adapting their size.

For young children, the most common type of diaper is what is called an all-in-one diaper, which comprises an absorption body enclosed in an outer cover and which is fastened together at the sides across the child's hips. The fastening is usually done with the aid of special fastening devices arranged on securing tabs. The fastening devices generally used are pressure-sensitive adhesive, or hook-and-loop devices. The securing tabs are in most cases secured on the rear portion of the diaper, at the side edges and near the rear waist edge of the diaper, and are passed forwards across the front portion of the diaper and secured to the latter. The diaper is generally provided with some type of receiving surface for the fastening device on the securing tabs. For adhesive securing tabs, some type of reinforcement of the outer cover of the diaper is used, for example in the form of a plastic strip which permits fastening and opening without breaking. Securing tabs with hook-and-loop devices are most often provided with the male parts (hook devices) of the hook-and-loop device and are secured to a corresponding female part, which can be a nonwoven surface with fibre loops in which the hooks can be securely hooked. The known securing tabs permit a certain adjustment of the fit and size of the diaper, but they are not completely satisfactory in this respect. In particular, both the body shape and girth can vary considerably between different adult users, and the known fastening devices have only a limited capacity for adjustment.

Another type of diaper which is commonly used on heavily incontinent adults is a diaper supported by a belt. Such diapers have a separate or integrated belt which is secured around the user's waist and from which the absorption body of the diaper is suspended. A diaper with an integrated belt usually has one half of the belt secured to the rear end of the diaper and protruding from side edges of the diaper. When the diaper is applied, the belt is secured around the user's waist with the diaper hanging down over the user's rear area. Thereafter, the front portion of the diaper is guided forwards between the user's legs and up across the stomach and is finally secured to the belt across the user's stomach. If the belt is designed to permit fastening across its entire width, it is possible to some extent to adjust the size of the diaper by virtue of the fact that the length or "pelvic dimension" can be varied depending on whether the diaper is secured near the bottom edge or top edge of the belt. However, this possibility of adjustment is very often insufficient, which means that even belt diapers have to be supplied in a number of different sizes.

Alternatively, a belt diaper can be supported by a separate belt. Such a diaper is preferably applied more or less like a diaper with an integrated belt. Thus, the diaper is secured with some type of fastening device to a rear part of the belt, after which the belt is fastened round the user's waist. Thereafter, the free end of the diaper is guided forwards and upwards across the user's stomach and is secured to the belt so that the diaper and the belt together assume a shape similar to briefs. A belt diaper with separate belt permits a slightly greater degree of size adjustment than a diaper with integrated belt. In addition, the belt can be designed so that it can be reused. However, these belt diapers too are still not sufficiently variable to satisfy the need for different sizes of diaper for different users.

OBJECT AND SUMMARY

There therefore remains a need for an absorbent article which can be fastened together in a briefs shape and in which the fastening devices permit a high degree of adjustment of the size and fit of the article.

In accordance with an embodiment of the invention, an absorbent article of the type discussed in the introduction has been obtained, namely comprising a fastening arrangement for fastening the absorbent article together. The fastening arrangement comprises a material strip with a longitudinal direction and a transverse direction, and with a first short end and a second short end, the first short end being firmly anchored in the absorbent article and the material strip comprising a fastening device.

An embodiment according to the invention is primarily distinguished by the fact that the fastening arrangement is an extendable fastening arrangement formed by the material strip being folded in a Z along two transversely extending fold lines which divide the material strip into a first end portion at the first short end, a second end portion at the second short end, and a middle portion between the end portions, and the first end portion of the material strip is secured to the middle portion by a first breakable attachment, and the second end portion of the material strip is secured to the middle portion by a second breakable attachment, and the fastening device is arranged on the second end portion of the folded material strip, on a surface directed away from the middle portion.

A firm anchoring signifies a permanent attachment which is not intended to be broken, either under the effect of the forces which arise during use of the absorbent article or by active pulling apart. A firm anchoring cannot normally be broken without surrounding material being destroyed.

A fastening arrangement according to an embodiment of the invention can assume two different fastening positions and affords the possibility of choosing between the different fastening positions. In the first fastening position, the fastening arrangement is used in the folded-together state defined above. To obtain the second fastening position, it is necessary to break the breakable attachments which fix the Z-folded material strip of the fastening arrangement in the folded state. This has to be done actively by the person fastening the absorbent article round the user's trunk. When the attachments have been broken, the material strip is unfolded to its full length, which means that the fastening devices have a much greater reach than in the folded-up state of the fastening arrangement. The different fastening positions can be used by the carer to adapt the size and fit of the absorbent article individually for each person receiving care.

When the absorbent article is an all-in-one diaper, the possibility of extending the fastening arrangements means that the width of the diaper can be regulated within a greater interval than was previously possible. An absorbent article in the form of a belt diaper instead acquires greater adaptability in the longitudinal direction, as a result of which the diaper can be used for a larger group of users with different pelvis lengths, i.e. different distances between crotch and waist. A belt diaper can of course also be adjustable in terms of its waist circumference if the waist band is provided with a Z-folded fastening arrangement in accordance with the invention.

The absorbent article can advantageously be a belt diaper with an elongate absorption part and a belt which supports the absorption part. The absorption part advantageously comprises an absorption body enclosed in a covering, said covering being formed for example by an inner liquid-permeable cover sheet and an outer liquid-impermeable backing sheet. Moreover, the absorption part can be provided with elastic devices along the side edges, by which means elastic leg openings are obtained.

According to one embodiment, the absorption part has a first end portion which is firmly anchored in the belt, the first end portion preferably being a rear end portion, and a second end portion, and the extendable fastening arrangement is firmly anchored on the second end portion and is designed to be secured on the belt.

The extendable fastening arrangement on the absorption part can extend in the transverse direction of the article along a greater or lesser part of an end edge of the absorption part. In such an embodiment, the fastening arrangement can have a greater extent in the transverse direction than in the longitudinal direction. When only one fastening arrangement is used, this is preferably placed at the end edge, centrally on the absorption part.

It is however preferable that at least two Z-folded extendable fastening arrangements are firmly anchored on the second end portion and are designed to be secured on the belt. When the article has two extendable fastening arrangements, these are preferably placed symmetrically on each side of a longitudinal centre line through the article, in the area between the end edges and side edges of the absorption part.

According to another embodiment, the absorption part and the belt are separate parts of the belt diaper which, during use, are fastened together to give a unit which looks like a pair of briefs. Such a belt diaper expediently has one or more extendable, Z-folded fastening arrangements on at least one end edge of the absorption part. The belt can be a reusable belt which can be used over again with new absorption parts. Alternatively, the belt can be of the disposable type and, like the absorption part, is discarded after use. In such an embodiment, the fastening devices on the fastening arrangement or fastening arrangements at one end edge can be of a type which permits permanent attachment of the fastening devices on the belt. However, it is an advantage if the fastening arrangement or fastening arrangements on at least one end edge permit release and, if appropriate, reattachment of the fastening devices on the belt. Such a design facilitates both adjustment of the fastening of the diaper and removal of the diaper after use.

The fastening arrangement or fastening arrangements according to the invention can either be arranged on the inside of the absorbent article, which is the side facing towards the user during use, or on the outside of the article. For belt diapers, it is generally preferred to arrange the fastening arrangement or fastening arrangements on the inside of the diaper, since in this way it is easy to secure the absorption part on the outside of the belt without any special manoeuvring. However, it is possible instead to arrange the fastening arrangements on the outside of the absorption part. In such an embodiment, the fastening devices are secured on the inside of the belt. For belt diapers with a separate belt, where rear fastening devices are first secured to the belt before the belt is arranged round the user's waist, there is no disadvantage in arranging these rear fastening devices on the outside of the absorption part. It can even be an advantage that in this connection the belt holds the absorption body pressed against the user's body during use. Another advantage of arranging the fastening arrangements on the outside of the absorbent article is that there is less risk of chafing or other types of discomfort, because the fastening arrangements are kept at a distance from the user's body. This is a particular advantage when using mechanical fastening devices such as hook-and-loop devices, which can be stiff and hard, with a chafing surface.

The belt too can be provided with one or more extendable, Z-folded fastening arrangements designed for fastening the belt round a user's waist. Such an embodiment means that the width of the diaper can be adapted to the user's girth.

The article may additionally comprise a further fastening arrangement in the form of a double-folded securing tab which is formed by an elongate material strip having a first end portion which is firmly anchored on the absorbent article, and a second end portion which is folded in against the first end portion and secured to this by a releasable attachment, and a fastening device is arranged on the second end portion, on that surface directed towards the first end portion. Such a securing tab provides for additional fastening, if so desired. The securing tab can be left in its folded state and then does not contribute to the fastening of the absorbent article. If the releasable attachment is broken, however, the fastening device is exposed and the securing tab can be used as a complement to the article's other fastening arrangements. For example, such a securing tab can be used to avoid gaps occurring between a belt and an absorption part.

The invention can also be applied to all-in-one diapers. In this case, the absorbent article is a diaper with two end edges and two side edges and having two end portions and an intermediate crotch portion, and with an extendable fastening arrangement firmly anchored to each side edge on the one end portion, the fastening arrangements being designed to cooperate with a receiving device on the second end portion.

The breakable attachments on the Z-folded, extendable fastening arrangement according to the invention, or on the double-folded securing tab, can comprise breakable welds. It is further possible to produce breakable attachments in the form of breakable adhesive seams. A suitable adhesive for producing such seams is a dry structural adhesive which is not tacky after breaking the seam. One example of such an adhesive is Dispomelt® 2000. The breakable seams should have sufficient strength to be able to hold the Z-folded fastening arrangement together in the folded state when the carer chooses not to unfold the fastening arrangement. At the same time, the seams should be able to be broken easily by manual force if the full length of the fastening arrangements is to be used. The person skilled in the art will, given his knowledge of the adhesive strength of different adhesives and the tensile and shearing forces which occur during use of a diaper, have no difficulty in producing seams with the correctly adapted seam strength.

It is of course also possible to use types of fastening devices other than adhesive fastening devices, for example various types of mechanical fastening devices such as hook and eyelet, button and button hole, press studs, and hook-and-loop devices. Particular preference is given to hook-and-loop devices here. By hook-and-loop devices we mean all types of fastening devices in which a male part provided with hooks or projections cooperates with and catches in a female part which is provided with eyelets or fibre loops. When using hook-and-loop devices, the male part is preferably arranged on the Z-folded extendable fastening arrangement and is designed to cooperate with a receiving surface constituting the female part of the hook-and-loop device. Combinations of mechanical and adhesive fastening devices are also conceivable within the scope of the invention.

The folded material strip in the fastening arrangement according to an embodiment of the invention preferably consists of a flexible material with high tensile strength. Suitable materials are plastic film, nonwovens and various types of laminates of these materials. In the case where the fastening arrangement comes to bear against the user's skin during use, it is expedient that the material in the material strip has a soft surface on the side facing towards the user. In addition, it may be expedient for the material to be breathable, i.e. allow moisture and water vapour to pass through. Nonwoven materials generally have a soft surface, let moisture pass through and do not stick to the skin. It is also expedient that the material strip is easily pliable and has soft edges, so that there is minimal risk of chafing of the user's skin. The material of the material strip can be substantially inelastic so that it does not stretch during use. Alternatively, the material can be stretchable and is then preferably elastically stretchable. Such an embodiment affords the possibility of continuous adjustment of the length of the material strip during use of the absorbent article.

To facilitate release of the breakable attachments, the fastening arrangement can be provided with a grip tab at the second short end of the material strip. Such a grip tab can expediently be formed by an edge area of the material strip which is free from bindings.

The fastening arrangement can be secured to a cover sheet of the absorbent article in such a way that the fastening arrangement, in its folded state, is accommodated completely within the surface of the cover sheet. Alternatively, the fastening arrangement can be firmly anchored at an edge of the absorbent article, so that the fastening arrangement protrudes outside the edge of the article even in the folded state. In such an embodiment, the fastening arrangement can be firmly anchored on a cover sheet of the article, or between the cover sheets. The fastening arrangement can of course be firmly anchored in some component located between the cover sheets. Attachment is expediently made by adhesive bonding, welding or sewing.

DESCRIPTION OF THE FIGURES

The invention will be described in more detail below with reference to the embodiments shown on the attached drawings, in which.

DETAILED DESCRIPTION OF THE PREFERRED EMBODIMENTS

Figure 1:
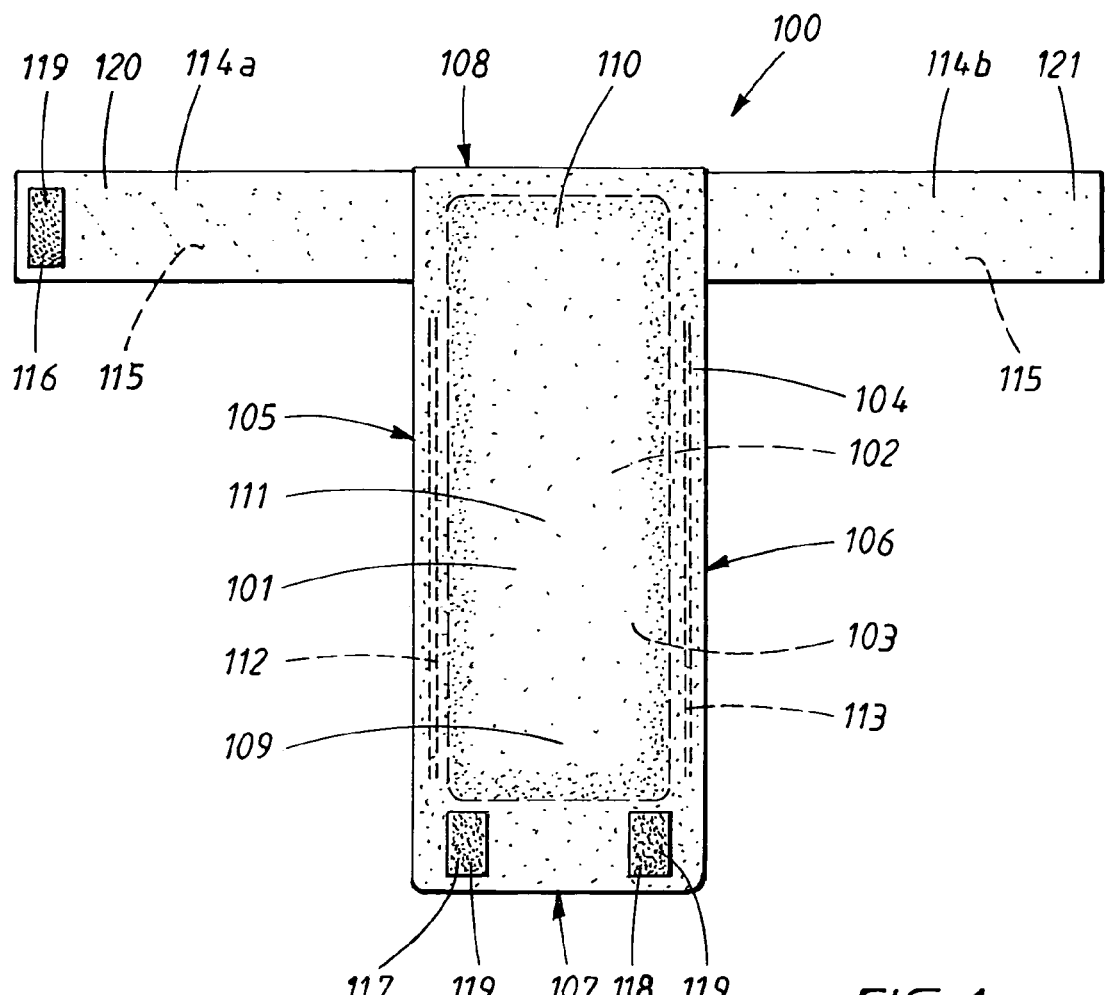
FIG. 1 shows a diaper according to an embodiment of the invention provided with a belt.
Figure 2:
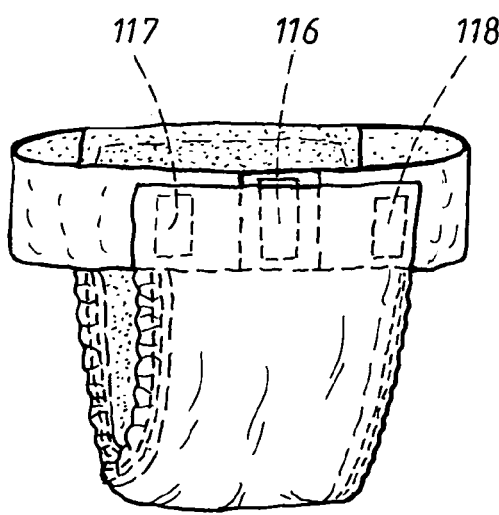
FIG. 2 shows the diaper from FIG. 1 in an assembled state.

FIGS. 1 and 2 show a diaper 100 with a substantially rectangular planar shape. The diaper 100 is shown from the side which is intended to face towards the user during use. The diaper comprises in a conventional manner a liquid-permeable covering sheet 101, a liquid-impermeable covering sheet 102, and an absorption body 103 enclosed between the covering sheets 101, 102.

The liquid-permeable covering sheet 101 has the same shape as the absorption body 103. The liquid-impermeable covering sheet 102 is also shaped like the absorption body. However, the covering sheets 101, 102 have a slightly greater planar extent than the absorption body 103 and form a connecting edge 104 which protrudes around the periphery of the absorption body 103. The covering sheets 101, 102 are connected to one another around the absorption body, for example by adhesive, sewing, or welding by heat or ultrasound. Moreover, one or both of the covering sheets 101, 102 can be connected to the absorption body 103, for example by adhesive, needling, sewing, or by welding with heat or ultrasound.

The liquid-permeable cover sheet 101 is of a conventional type and can thus consist of any liquid-permeable material suitable for the purpose. Examples of such materials are various types of thin nonwoven material, perforated plastic films, mesh material, liquid-permeable foam material, or similar. The liquid-permeable cover sheet 101 can be made up of two or more different materials in order to permit different functions of the cover sheet. For example, it is customary to arrange a liquid-transporting layer inside a liquid admission layer. It is also known to arrange different types of materials on different parts of the surface of the diaper facing towards the user during use. Thus, a material with a good admission capacity can advantageously be arranged at the portion of the diaper which is expected to be wetted first by most of the body fluid, while portions of the covering sheet located at a distance from the first wetted area can be designed with a barrier function in order to prevent absorbed liquid from leaking out of the diaper.

Nor is it essential to the invention that the liquid-permeable cover sheet 101 is a separate sheet of material, and instead the cover sheet 101 can be a surface of the absorption body 103 of the diaper 100.

The liquid-impermeable covering sheet 102 can also be made of any available suitable material. Especially advantageous materials are thin plastic films, liquid-impermeable nonwoven material, or layered material which has been coated with liquid-impermeable material such as wax, resin, adhesive or the like. It is also possible to use liquid-impermeable material laminates. For example, it may be desirable to provide the reverse of the diaper with an outer sheet of textile character, for example a nonwoven sheet. Such a nonwoven material provides a soft, skin-friendly textile surface and affords advantages such as a high level of user comfort, a high degree of friction and, consequently, a better hold on the clothing worn over the diaper. In addition, a textile surface is often considered to have an aesthetically pleasing appearance. It is also an advantage if the liquid-impermeable covering sheet 102 is breathable, i.e. lets gas and water vapour pass through the sheet.

The absorption body 103 can also be designed in a conventional manner and with conventional materials. Suitable absorbent materials for use in the absorption body 103 are, for example, cellulose fluff pulp, absorbent bound fibre sheets, tissue layers, absorbent foam, peat or the like. The absorption body 103 can also advantageously contain superabsorbent polymers, i.e. polymers which are able to absorb many times their own weight of liquid and form a liquid-containing gel. Superabsorbents are generally present in the form of particles, flakes, fibres, granules or the like. The superabsorbent material can be present alone or in combination with other absorbent material and applied as layers, or in the form of a mixture with other materials such as cellulose fibres or synthetic fibres.

As has already been mentioned, the diaper 100 in FIGS. 1 and 2 is substantially rectangular in shape and has two straight side edges 105, 106 and two similarly straight end edges 107, 108. The diaper can be divided into a front portion 109, a rear portion 110, and an intermediate crotch portion 111.

Elastic devices 112, 113 are arranged along the side edges 105, 106 and form leg elastics when the diaper 100 is in use. Suitable elastic devices are various types of elastic threads, bands, elastic nonwovens, elastic foam material, or similar.

The diaper 100 is further provided with a two-part waist belt 114a,b which is arranged with a belt half 114a,b protruding at right angles from each side edge 105, 106 at the rear end edge 108 of the diaper. The belt halves 114a,b consist of strips of a soft and flexible material. Suitable materials are nonwoven materials or material laminates of one or more layers of nonwoven, plastic film or the like. Thus, the belt halves 114a,b can comprise material layers whose main purpose is to give the waist belt some desired property, such as improved softness and comfort, increased tensile strength, a more aesthetically pleasing appearance, a certain elasticity, a certain absorption capacity, etc. The waist belt 114a,b is additionally provided with loop devices 115 arranged on the outside of the waist belt, i.e. on the surface facing away from the user during use. In FIG. 1, the outside is directed away from the observer. Such loop devices 115 can be formed in a woven, knitted or cast material or can consist of fibre loops in a nonwoven material. As in the example shown, the loop devices 115 can be arranged across the whole outside of the waist belt 114a,b or can be placed only in special fastening areas intended for fastening to corresponding hook devices.

To ensure that the diaper 100, at the time of use, can be fastened together to give a garment similar to briefs, the diaper is additionally provided with fastening devices 116, 117, 118 which have hook devices 119. A fastening device 116 provided with hooks is arranged at the free end 120 of one belt half 114a, on the surface directed away from the loop device 115. Fastening arrangements 117, 118 are also arranged at the corners between the side edges 105, 106 and the front end edge 107. The fastening arrangements 117, 118 have hook-like fastening devices 119 on the surface which is directed towards the viewer of FIG. 1, i.e. the surface facing towards the user when the diaper is in use.

In this context, hook devices is meant to cover all existing types of hooks and projections which can hook into the loops or fibre loops on the loop device 115.

At the time of use, the diaper 100 is fastened round the lower part of a user's trunk and assumes the form shown in FIG. 2. It is fastened together by the free end portions 120, 121 of the two halves 114a,b of the waist belt being passed round the user's waist and by the hooked fastening device 116 on one belt half 114a of the waist belt being secured in the fastening loops on the other belt half 114b. The front end edge 107 of the diaper is then passed forwards between the user's legs and secured by means of the hooked fastening devices 119 on the fastening arrangements 117, 118 against the loop device 115 on the waist belt 1114a,b.

Figure 3A:
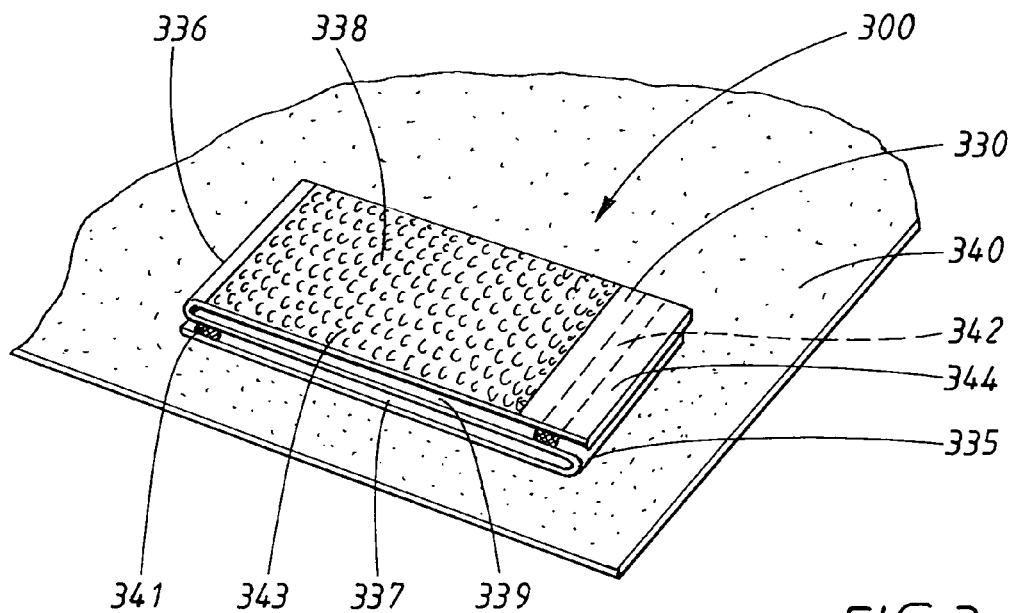
FIG. 3a shows a detail of a fastening arrangement on an absorbent article according to an embodiment of the invention, in the folded-up state.
Figure 3B:
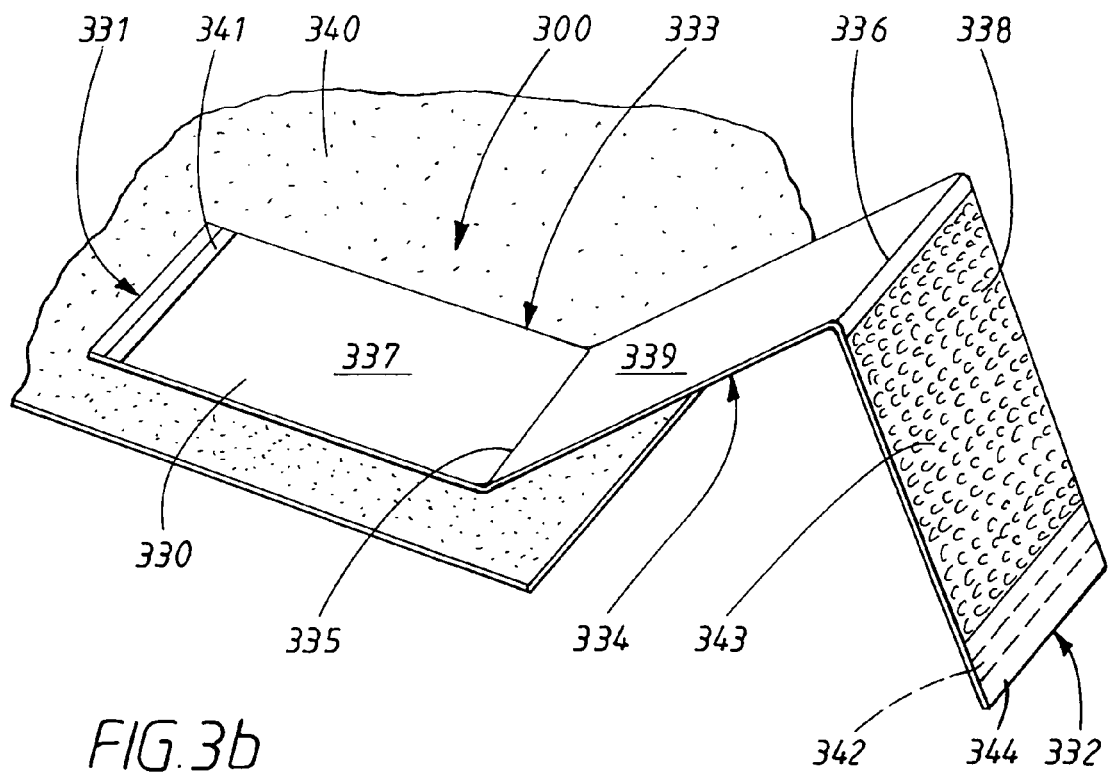
FIG. 3b shows a detail of a fastening arrangement on an absorbent article according to an embodiment of the invention, in the unfolded state.

FIGS. 3a and 3b show enlarged views of a fastening arrangement 300 according to an embodiment of the invention. In FIG. 3a, the fastening arrangement 300 is seen fixed in a Z-folded state, and in FIG. 3b the fastening arrangement is shown in a partially unfolded state. The fastening arrangement 300 comprises a material strip 330 having a first end edge 331, a second end edge 332, a first side edge 333, and a second side edge 334. Moreover, the material strip 330 is divided by a first fold line 335 and a second fold line 336 into a first end portion 337, a second end portion 338, and a middle portion 339 between the end portions 337, 338. The first end portion 337 is firmly anchored in an absorbent article 340, for example by adhesive bonding or welding.

In the folded state in FIG. 3a, the middle portion 339 of the material strip 330 is secured to the first end portion 337 by a first breakable attachment 341. The attachment 341 can be adhesive, for example in the form of a string of glue, or the attachment can be produced by means of welding. In FIGS. 3a and b, the attachment 341 is shown as a rectangular area at the first end edge 331 of the material strip 330. However, it is alternatively possible to arrange a binding pattern across a greater part of the mutually facing surfaces of the first end portion 337 and the middle portion 339. Such a binding pattern can of course also be arranged across all the bound surfaces.

In a corresponding manner, mutually facing surfaces of the middle portion 339 and the second portion 338 are bound together by means of a second breakable attachment 342.

The fastening arrangement 300 is provided with a fastening device 343. The figure shows, by way of example, a hook-and-loop type surface with hook devices. However, it is also possible to use any other type of fastening device, such as touch-and-close type surfaces with loop devices, glue, buttons, press studs, hooks and loops, etc.

At the other end edge 332 there is an area which is free from fastening devices 343 and attachments. This area serves as a grip tab 344 when the fastening arrangement is to be unfolded to its second fastening position.

When the fastening arrangement 300 is used to fasten together an absorbent article, the fastening arrangement can be used in the folded state shown in FIG. 3a. However, if the user of the absorbent article has a body shape and/or body size requiring a greater reach of the fastening arrangement, the breakable attachments 341, 342 can instead be pulled apart and the fastening arrangement unfolded to the full length of the material strip, as is shown in FIG. 3b. For the belt diaper 100 shown in FIGS. 1 and 2, this means that the diaper has a greater extent down about the user's crotch region when the fastening arrangements 117, 118 placed at the front edge 107 of the diaper are unfolded. In a corresponding manner, the belt parts 114a,b of the diaper 100 can be made to extend round a larger person's waist when the fastening arrangement 116 placed on the belt is unfolded enabling traverse adjustment of the belt.

Figure 4:
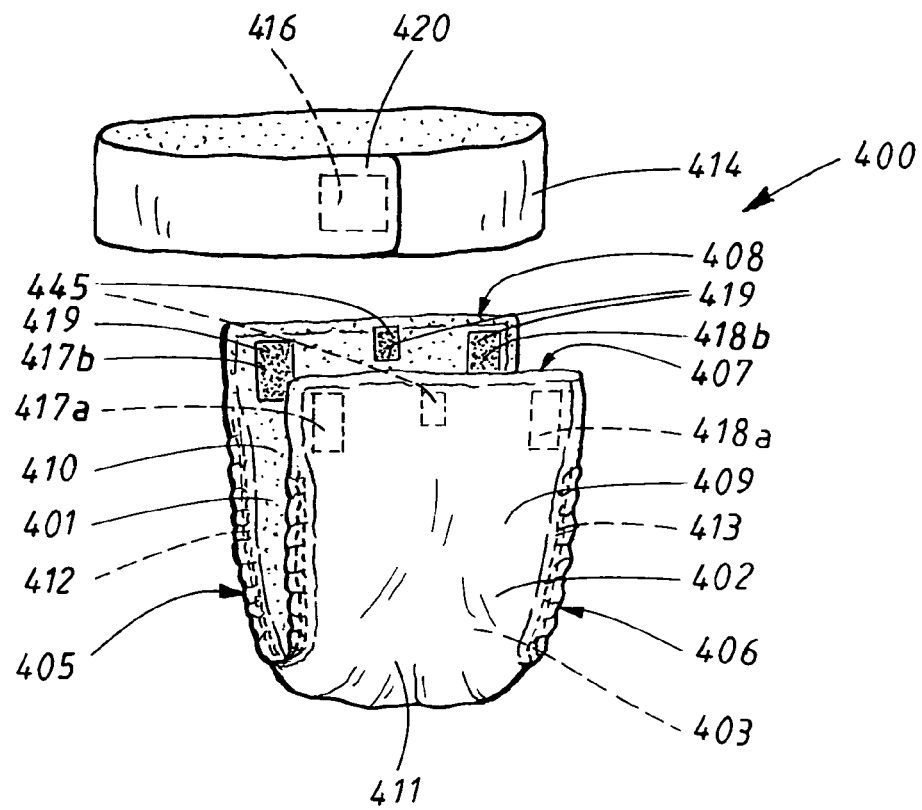
FIG. 4 shows a diaper, provided with belt, according to an alternative embodiment of the invention.

The diaper 400 shown in FIG. 4 is shown in a curved state together with a completely continuous waist belt 414 and correspondingly comprises a liquid-permeable covering sheet 401, a liquid-impermeable covering sheet 402, and an absorption body 403 enclosed between the covering sheets 401, 402. The diaper 400 is rectangular, with a front end portion 409 and rear end portion 410, and an intermediate narrower crotch portion 411. Moreover, the diaper has two side edges 405, 406 which form openings about a user's legs when the diaper is arranged on the user, and a front end edge 407 and rear end edge 408 which together form the waist edge of the diaper during use. The diaper 400 additionally has elastic devices 412, 413 arranged along the curved side edges 405, 406 and intended to gather the diaper together around the user's legs so that a tight seal is obtained around the legs.

To ensure that the diaper 400, when in use, can be fastened together to give a garment similar to briefs, the diaper is additionally provided with fastening arrangements 416,417a,b, 418a,b having fastening devices 419. These fastening device may be of the type disclosed in FIGS. 3a and 3b. Fastening arrangements 417a,b, 418a,b are arranged at the corners between the side edges 405, 406 and the front end edge 407 and rear end edge 408. The fastening arrangements 417a,b, 418a,b have hooked fastening devices 419 intended to be secured against the outside of the waist belt 414.

Figure 5A:
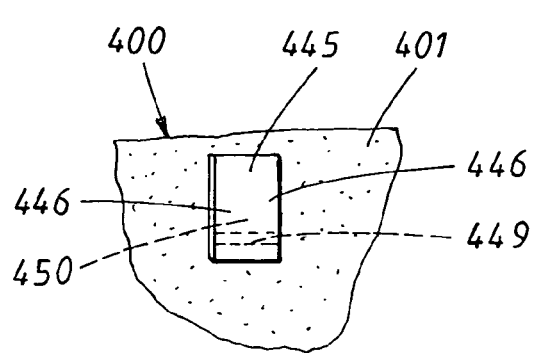
FIG. 5a shows a detail of a fastening device on the diaper from FIG. 4, in the folded-up state.
Figure 5B:
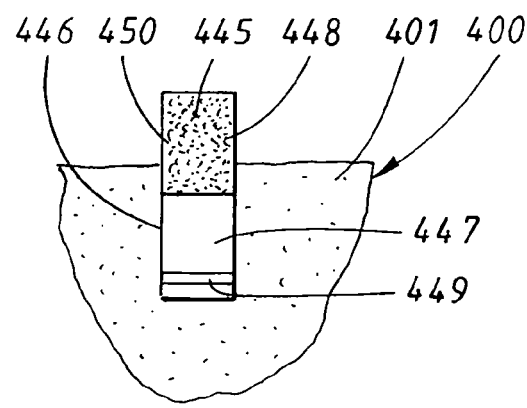
FIG. 5b shows a detail of a fastening device on the diaper from FIG. 4, in the unfolded state.

The diaper 400 additionally comprises a further fastening arrangement in the form of a single-folded securing tab 445 at each end edge 407, 408. As is shown in detail in FIGS. 5a and b, the securing tab 445 is formed by an elongate material strip 446 having a first end portion 447 firmly anchored on the diaper 400 and a second end portion 448 folded in against the first end portion 447 and secured to the latter by a releasable attachment 449, for example in the form of an adhesive seam, or a weld. A fastening device 450 is arranged on the second end portion on the surface which, on the folded material strip 446, is directed towards the first end portion. Such a securing tab, if so desired, provides for additional fastening. The securing tab can be left in its folded state and then does not contribute to the fastening of the diaper 400. However, if the releasable attachment is broken, as is shown in FIG. 5b, the fastening device 450 is exposed and the securing tab can be used as a complement to the other fastening arrangements 417a,b, 418a,b of the article. The securing tab 445 can be used to prevent gaps from occurring between the belt and the absorption part of the diaper.

When the diaper shown in FIG. 4 is applied, the procedure is essentially the same as when applying the diaper in FIGS. 1 and 2. The rear portion 410 of the diaper is preferably first secured to the waist belt 414 by the rear fastening arrangements 417b, 418b. These can be in the folded state or can be unfolded if so desired. The waist belt 414 is thereafter secured round the user's waist by means of the fastening arrangement 416, and finally the front portion 409 of the diaper is passed forwards and upwards between the user's legs and is secured on the waist belt 414 by the front fastening arrangements 417a, 418a. Like the fastening arrangement 416 on the waist belt 414, the front fastening arrangements 417a, 418a can also be used in their folded state or in their unfolded state.

Figure 6:
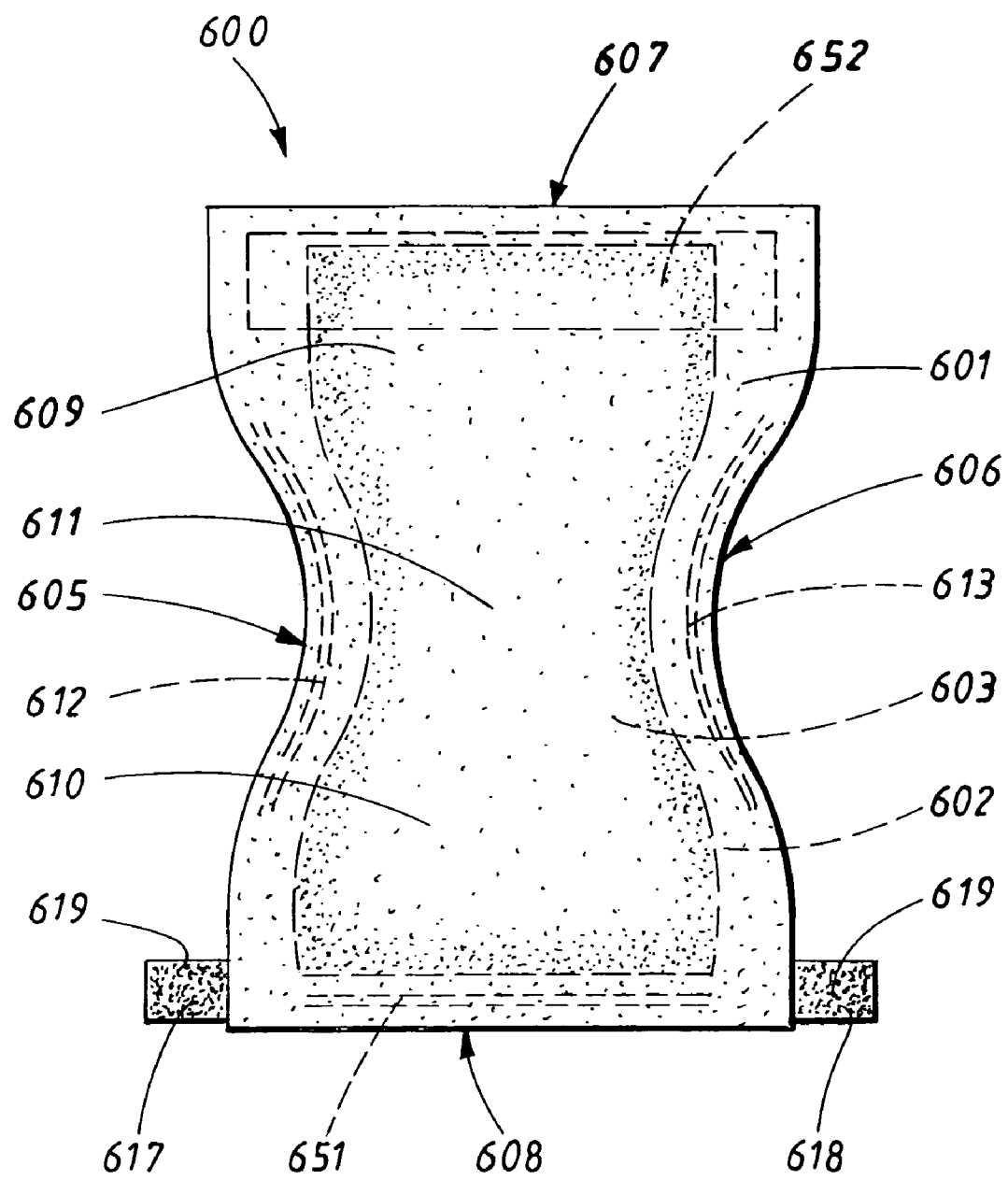
FIG. 6 shows an all-in-one diaper according to an embodiment of the invention.

The diaper 600 in FIG. 6 is shown form the side which faces towards the user during use and is of the all-in-one type. The diaper has in principle the same design as the previously described diapers and comprises a liquid-permeable covering sheet 601, a liquid-impermeable covering sheet 602, and an absorption body 603 enclosed between the covering sheets 601, 602. The diaper 600 is substantially hourglass-shaped, with a front end portion 609 and rear end portion 610, and an intermediate narrower crotch portion 611. The diaper also has two curved side edges 605, 606 which are designed to form rounded openings around a user's legs when the diaper is arranged on the user, and a front end edge 607 and rear end edge 608 which together form the waist edge of the diaper 600 during use. The diaper 600 additionally has elastic devices 612, 613 arranged along the curved side edges 605, 606 and intended to gather the diaper around the user's legs so that a tight seal is obtained around the legs. A further elastic device 651 is arranged along the rear end edge 608 of the diaper and forms a waist elastic when the diaper is in use.

To ensure that the diaper can be fastened together to give a garment similar to briefs, Z-folded extendable fastening arrangements 617, 618 are arranged so that even in their folded state they protrude from the side edges 605, 606 at the rear end edge 608. The fastening arrangements 617, 618 are shown secured on the liquid-permeable covering sheet 601. However, it is possible to instead secure the protruding fastening arrangements 617, 618 on the liquid-impermeable covering sheet 602, or between the covering sheets 601,602.

When applying the diaper shown in FIG. 6, the diaper is arranged with the crotch portion 611 between the user's legs and the front and rear portions 609, 610 are guided upwards and fastened together with the aid of the extendable fastening arrangements 617, 618. The fastening arrangements 617, 618 are secured on a receiving area 652 arranged on the front portion. As in the previously described embodiments, the fastening arrangements 617, 618 can be used either in their folded state, as is shown in FIG. 6, or when folded out to their full length. Instead of using a special receiving area 652 for the fastening arrangements 617, 618, it is possible to secure the fastening arrangements 617, 618 directly on the outer face of the diaper. If the fastening arrangements 617, 618 comprise fastening devices in the form of hook devices 619, it is expedient, in such an embodiment, for the outer face of the diaper to be a nonwoven material.

Figure 7A:
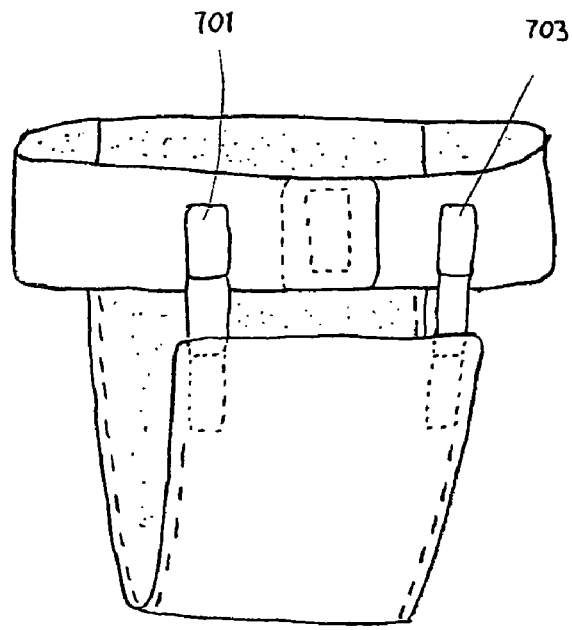
FIGS. 7a and 7b schematically show a diaper according to an embodiment of the invention with the breakable attachments affixed to the diaper and in the unfolded state.
Figure 7B:
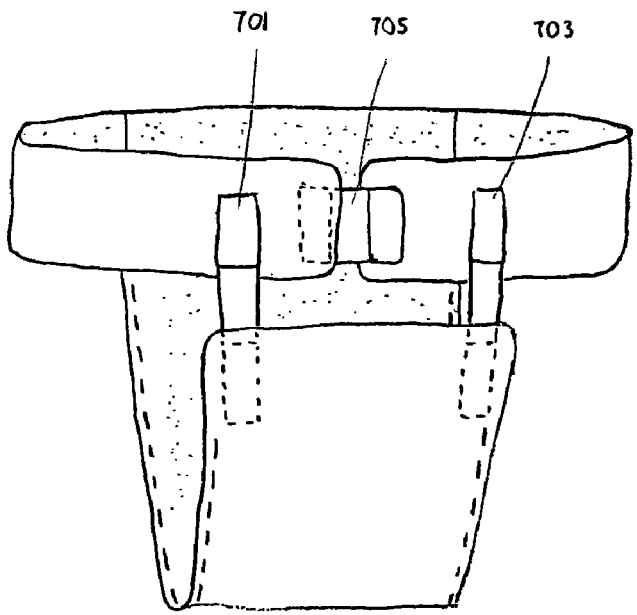

FIG. 7a schematically shows a diaper with z-fold fastening devices 701 and 703 broken apart and unfolded to the full length of the material strip. The diaper thus has a greater extent in the longitudinal direction. FIG. 7b schematically shows a diaper with z-fold fastening devices 701 and 703 broken apart and unfolded to the full length of the material strip. Further, FIG. 7*b* shows z-fold fastening device 705 broken apart and unfolded to the full length of the material strip. The diaper thus has a greater extent in the longitudinal direction and in the transverse direction of the diaper.

The invention is not to be considered as being limited by the illustrative embodiments described here. In particular, it is possible to vary the shape of the diapers described, and also the composition of the absorption body and other components of no importance for fastening.

The invention claimed is:

1. An absorbent article with a longitudinal direction and a transverse direction and with two end edges extending in the transverse direction and two side edges extending in the longitudinal direction, the article further comprising a fastening arrangement for fastening the absorbent article, said fastening arrangement comprising a material strip with a longitudinal direction and a transverse direction and with a first end and a second end, said first end of the material strip being firmly anchored to the absorbent article, and the material strip comprising a fastening device, the fastening arrangement is an extendable fastening arrangement formed by the material strip being folded in a Z along two fold lines extending transversely across the material strip and which divide the material strip into a first end portion at the first end, a second end portion at the second end, and a middle portion between the end portions, and the first end portion of the material strip is secured to the middle portion by a first breakable attachment, and the second end portion of the material strip is secured to the middle portion by a second breakable attachment, and the fastening device is arranged on the second end portion on a surface directed away from the middle portion when the material strip is in the folded state, wherein the article further comprises an elongate absorption part, said absorption part having a first end portion and a second end portion, wherein the extendable fastening arrangement is firmly anchored on one end portion of the absorption part and the extendable fastening arrangement is extendable in the longitudinal direction of the absorbent article the article further comprising a belt, wherein the extendable fastening arrangement is adapted to be secured to the belt, wherein the first end portion of the absorption part is firmly anchored to the belt, and the extendable fastening arrangement is firmly anchored to the second end portion, wherein the article further comprises a second extendable fastening arrangement which is firmly anchored to the second end portion of the absorption part and is adapted to be secured to the belt.

2. The absorbent article according to claim 1, wherein the article comprises a single-folded securing tab which is formed by an elongate material strip having a first end portion which is firmly anchored on the absorbent article, and a second end portion which is folded in against the first end portion and secured to this by a breakable attachment, and a fastening device is arranged on the second end portion on that surface directed towards the first end portion.

3. The absorbent article according claim 1, wherein the breakable attachments comprise breakable welds.

4. The absorbent article according to claim 1, wherein the breakable attachments comprise breakable adhesive seams.

5. The absorbent article according to claim 4, in which the adhesive seams are formed by a dry structural adhesive which is not tacky after breaking.

6. The absorbent article according to claim 1, wherein the fastening device comprises hook-and-loop fastening devices.

7. The absorbent article according to claim 6, in which the hook-and-loop fastening devices comprise hooks.

8. The absorbent article according to claim 6, in which the hook-and-loop fastening devices comprise loops.

9. The absorbent article according to claim 1, wherein the fastening arrangement comprises a grip tab on the second end portion of the fastening arrangement.

10. The absorbent article according to claim 1, wherein the material strip of the fastening arrangement is stretchable.

11. The absorbent article according to claim 1, wherein the material strip of the fastening arrangement is elastically stretchable.

12. An absorbent article with a longitudinal direction and a transverse direction and with two end edges extending in the transverse direction and two side edges extending in the longitudinal direction, the article further comprising at least two fastening arrangements for fastening the absorbent article, said fastening arrangements each comprising a material strip with a longitudinal direction and a transverse direction and with a first end and a second end, said first end of the material strip being firmly anchored to the absorbent article, and the material strip comprising a fastening device, each fastening arrangement is an extendable fastening arrangement formed by the material strip being folded in a Z along two fold lines extending transversely across the material strip and which divide the material strip into a first end portion at the first end, a second end portion at the second end, and a middle portion between the end portions, and the first end portion of the material strip is secured to the middle portion by a first breakable attachment, and the second end portion of the material strip is secured to the middle portion by a second breakable attachment, and the fastening device is arranged on the second end portion on a surface directed away from the middle portion when the material strip is in the folded state, wherein the article further comprises a belt with a longitudinal direction and a transverse direction and with two end edges extending in the transverse direction and two side edges extending in the longitudinal direction and an elongate absorption part, said absorption part having a first end portion and a second end portion, and at least one extendable fastening arrangement is firmly anchored on one end portion of the absorption part, is adapted to be secured to the belt, and is extendable in the longitudinal direction of the absorbent article, wherein the belt further comprises at least one extendable fastening arrangement that is firmly anchored on one end edge of the belt, is adapted to be secured to the second end edge of the belt, and is extendable in the transverse direction of the absorbent article.

13. An absorbent article with a longitudinal direction and a transverse direction and with two end edges extending in the transverse direction and two side edges extending in the longitudinal direction, the article further comprising a fastening arrangement for fastening the absorbent article, said fastening arrangement comprising a material strip with a longitudinal direction and a transverse direction and with a first end and a second end, said first end of the material strip being firmly anchored to the absorbent article, and the material strip comprising a fastening device, the fastening arrangement is an extendable fastening arrangement formed by the material strip being folded in a Z along two fold lines extending transversely across the material strip and which divide the material strip into a first end portion at the first end, a second end portion at the second end, and a middle portion between the end portions, and the first end portion of the material strip is secured to the middle portion by a first breakable attachment, and the second end portion of the material strip is secured to the middle portion by a second breakable attachment, and the fastening device is arranged on the second end portion on a surface directed away from the middle portion when the material strip is in the folded state, wherein the article further comprises an elongate absorption part, said absorption part having a first end portion and a second end portion, wherein the extendable fastening arrangement is firmly anchored on one end portion of the absorption part and the extendable fastening arrangement is extendable in the longitudinal direction of the absorbent article, the article further comprising a belt, wherein the extendable fastening arrangement is adapted to be secured to the belt, wherein the article further comprises a second extendable fastening arrangement, of which one is firmly anchored on the first end portion of the absorption part, and one is firmly anchored on the second end portion of the absorption part, wherein the article comprises four extendable fastening arrangements, of which two are firmly anchored on the first end portion of the absorption part and two are firmly anchored on the second end portion of the absorption part.

14. The absorbent article according to claim 13, wherein the article comprises a single-folded securing tab which is formed by an elongate material strip having a first end portion which is firmly anchored on the absorbent article, and a second end portion which is folded in against the first end portion and secured to this by a breakable attachment, and a fastening device is arranged on the second end portion on that surface directed towards the first end portion.

15. The absorbent article according claim 13, wherein the breakable attachments comprise breakable welds.

16. The absorbent article according to claim 13, wherein the breakable attachments comprise breakable adhesive seams.

17. The absorbent article according to claim 16, in which the adhesive seams are formed by a dry structural adhesive which is not tacky after breaking.

18. The absorbent article according to claim 13, wherein the fastening device comprises hook- and-loop fastening devices.

19. The absorbent article according to claim 18, in which the hook-and-loop fastening devices comprise hooks.

20. The absorbent article according to claim 18, in which the hook-and-loop fastening devices comprise loops.

21. The absorbent article according to claim 13, wherein the fastening arrangement comprises a grip tab on the second end portion of the fastening arrangement.

22. The absorbent article according to claim 13, wherein the material strip of the fastening arrangement is stretchable.

23. The absorbent article according to claim 13, wherein the material strip of the fastening arrangement is elastically stretchable.

* * * * *